US010835715B2

(12) United States Patent
Cruz, Jr. et al.

(10) Patent No.: US 10,835,715 B2
(45) Date of Patent: Nov. 17, 2020

(54) SYSTEM AND METHOD FOR LOCATING A CATHETER TIP

(71) Applicant: AngioDynamics VA LLC, Latham, NY (US)

(72) Inventors: Andres B. Cruz, Jr., Red Hill, PA (US); Mark S. Fisher, Sellersville, PA (US)

(73) Assignee: AngioDynamics VA LLC, Latham, NY (US)

( * ) Notice: Subject to any disclaimer, the term of this patent is extended or adjusted under 35 U.S.C. 154(b) by 166 days.

(21) Appl. No.: 15/670,460

(22) Filed: Aug. 7, 2017

(65) Prior Publication Data

US 2018/0036513 A1 Feb. 8, 2018

Related U.S. Application Data

(60) Provisional application No. 62/372,418, filed on Aug. 9, 2016, provisional application No. 62/371,892, filed on Aug. 8, 2016.

(51) Int. Cl.
| | |
|---|---|
| *A61M 25/01* | (2006.01) |
| *A61B 34/20* | (2016.01) |
| *A61B 5/0215* | (2006.01) |
| *A61B 5/021* | (2006.01) |
| *A61M 25/00* | (2006.01) |
| *A61B 5/06* | (2006.01) |

(52) U.S. Cl.
CPC ..... *A61M 25/0158* (2013.01); *A61B 5/02108* (2013.01); *A61B 5/02152* (2013.01); *A61B 5/065* (2013.01); *A61B 34/20* (2016.02); *A61M 25/0067* (2013.01); *A61B 5/061* (2013.01); *A61B 2034/2063* (2016.02); *A61B 2562/0204* (2013.01); *A61M 2025/0002* (2013.01); *A61M 2025/0166* (2013.01)

(58) Field of Classification Search
CPC .......... A61M 25/0158; A61M 25/0067; A61M 2025/0002; A61M 2025/0166; A61B 34/20; A61B 5/02108; A61B 5/02152; A61B 5/065; A61B 5/06; A61B 5/061; A61B 2034/2063; A61B 2562/0204; A61B 2034/2065
USPC .......................................................... 73/584
See application file for complete search history.

(56) References Cited

U.S. PATENT DOCUMENTS

| | | | | |
|---|---|---|---|---|
| 3,499,434 | A * | 3/1970 | Ullrich ................. | A61B 5/0215 600/483 |
| 5,453,576 | A * | 9/1995 | Krivitski .............. | A61B 5/0275 600/454 |
| 2002/0107445 | A1* | 8/2002 | Govari .................... | A61B 5/06 600/437 |
| 2012/0083702 | A1* | 4/2012 | Ingold, Jr. .............. | A61B 5/061 600/483 |
| 2017/0189124 | A1* | 7/2017 | Canfield ................ | A61B 6/541 |

(Continued)

*Primary Examiner* — Stephen D Meier
*Assistant Examiner* — Rose M Miller
(74) *Attorney, Agent, or Firm* — Peter Flora (57) ABSTRACT

A system for locating the tip of a catheter inside a human body is provided. The system includes a sound sensor for sensing the magnitude wave form generated by sound pressure as a PICC is progressed toward a heart of a patient. The systems also includes a monitor operably coupled to the sensor for measuring the magnitude of wave form generated by the sound sensor.

20 Claims, 9 Drawing Sheets

(56) References Cited

U.S. PATENT DOCUMENTS

| | | | |
|---|---|---|---|
| 2017/0215837 A1* | 8/2017 | Ramakrishna | A61B 8/085 |
| 2017/0333000 A1* | 11/2017 | Nystrom | A61B 5/0215 |

\* cited by examiner

SYSTEM AND METHOD FOR LOCATING A CATHETER TIP

CROSS REFERENCE TO RELATED APPLICATIONS

This application claims the benefit of U.S. Provisional patent application Ser. No. 62/371,892, filed on Aug. 8, 2016; and claims the benefit of U.S. Provisional patent application Ser. No. 62/372,418, filed on Aug. 9, 2016; the entireties of which are hereby incorporated by reference.

FIELD OF THE INVENTION

The present invention relates generally to a system and method for locating a catheter tip within a human body.

BACKGROUND OF THE INVENTION

Medical professionals commonly use catheters for gaining access to a target area within the human body. After the catheter tip is properly positioned at the target area, treatments such as chemotherapy, delivery of medication for pain therapy, and delivery of nutrition in patients who cannot swallow, can be administered. However, if the catheter tip is improperly positioned during insertion, or if the catheter tip migrates out of position after insertion, complications may arise, such as risks to patient safety, increased thrombosis, delays in delivery of therapy, catheter malfunction, and additional hospital costs.

The general standard for proper catheter insertion depends on the type of catheter and the type of treatment. For example, peripherally inserted central catheters, commonly referred to as PICC lines, are typically inserted into a vein in the arm and advanced through the venous system towards the superior vena cava. However, because PICC lines are advanced through the venous system to reach the superior vena cava, the PICC line tip may be inadvertently positioned in a non-target area, such as the internal jugular or subclavian vein. Further, even if a PICC line is properly inserted, the catheter tip could later shift out of position. Therefore, being able to determine the direction and approximate location of the PICC tip is essential for patient safety.

Catheter tip location techniques have improved the ability of medical professionals to verify the location of the catheter tip. One technique involves using an audio sensor that detects an audio signal and transmits it to a processor. The processor determines whether the audio signal corresponds to a target location of the catheter tip. Another technique uses electromagnetic detection and a stylet having an electromagnetic sensor placed inside the lumen of the catheter tip. Electromagnetic systems use an external device positioned directly over the internal target area for generating a magnetic field outside of the body. The electromagnetic sensor on the stylet is then inserted into the body through the catheter lumen and measures when the magnetic flux is at its greatest. A monitor indicates to the user when the electromagnetic sensor on the stylet is centered underneath the external device. Other techniques use ultrasound to determine catheter tip location.

However, the systems and methods described above have deficiencies. For example, interpreting the image using ultrasound can be difficult. Electromagnetic detection may have measurement accuracy disrupted by electromagnetic interference. Additionally, electromagnetic sensing technology may be cost prohibitive.

Therefore, what is needed is a new system and method of locating a catheter tip within a human body that minimize the deficiencies noted above.

BRIEF SUMMARY OF THE INVENTION

The present invention addresses the deficiencies outlined above. In one aspect of the invention, a PICC is fitted with a sound sensor and is guided towards the heart of a patient for placement in the superior vena cava. Location of the catheter tip is determined based on the magnitude of sound as the catheter tip nears the heart, as hereinafter described.

In another aspect of the invention a sound sensor is housed within a sealed chamber that is filled with saline and that may be positioned on the saline column of the PICC. The sound of the heart is conducted through the catheter to the sealed chamber and propagated therewithin. The sound sensor senses the magnitude of the wave form generated by sound pressure. The sound sensor may be in communication with monitoring means having a display that graphically displays the sensed sound. As the PICC is progressed toward the superior vena cava the magnitude of the sound increases. A drop or decrease in the magnitude of the sound may indicate that the PICC has inadvertently been positioned in a non-target area or has shifted out of position or has been obstructed.

In another aspect of the invention, one or more acoustic sound emitters may be placed at locations on the patient's body. A first acoustic beacon emitter may be placed directly over the patient's heart to track the catheter tip as it nears the superior vena cava. The first acoustic beacon emitter may utilize a specific frequency or sound to enable the user to distinguish it from other emitters. Second and third acoustic beacons emitters may be placed on positions that are typically considered to be misplacement positions. Second and third emitters may also be used as triangulation devices by sending timed pulses or other signals that can be calculated by the sensor system to obtain the location of the catheter tip. Acoustic beacons emitters emit an acoustic beacon signal that are detected by the sound sensor and displayed graphically on the display unit of the monitoring means.

BRIEF DESCRIPTION OF THE DRAWINGS

For a better understanding of the invention, and to show how the same may be carried into effect, reference will now be made, by way of example, to the accompanying drawings, in which.

DETAILED DESCRIPTION OF THE INVENTION

Figure 1:
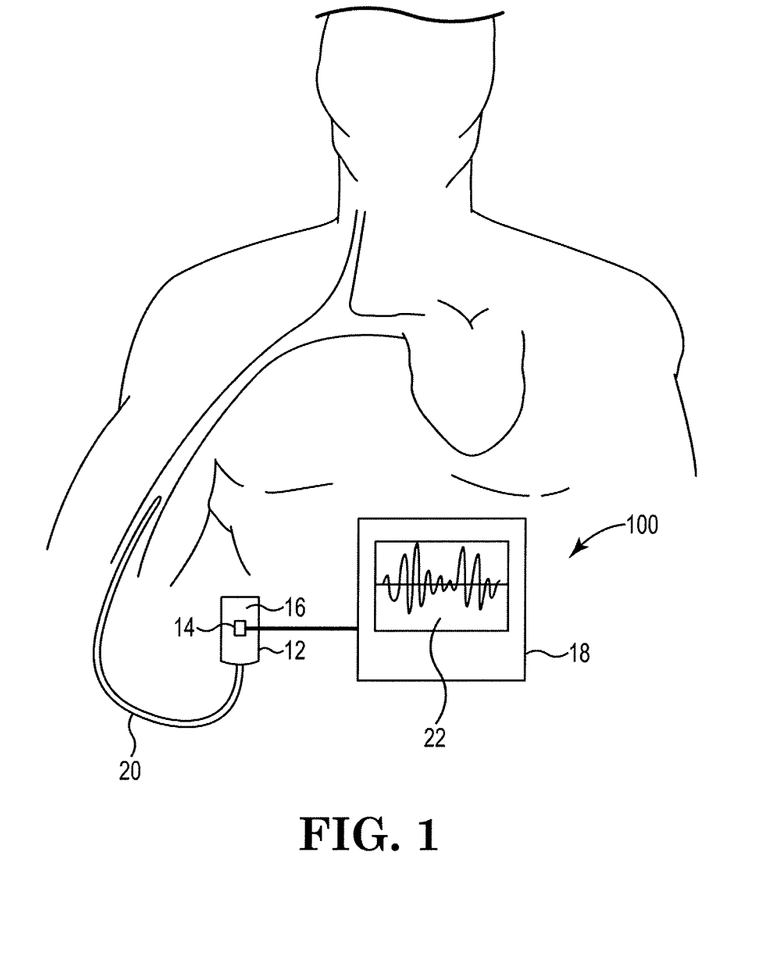
FIG. 1 depicts the device of the present invention coupled to a catheter that is being advanced towards the superior vena cava.
Figure 4:
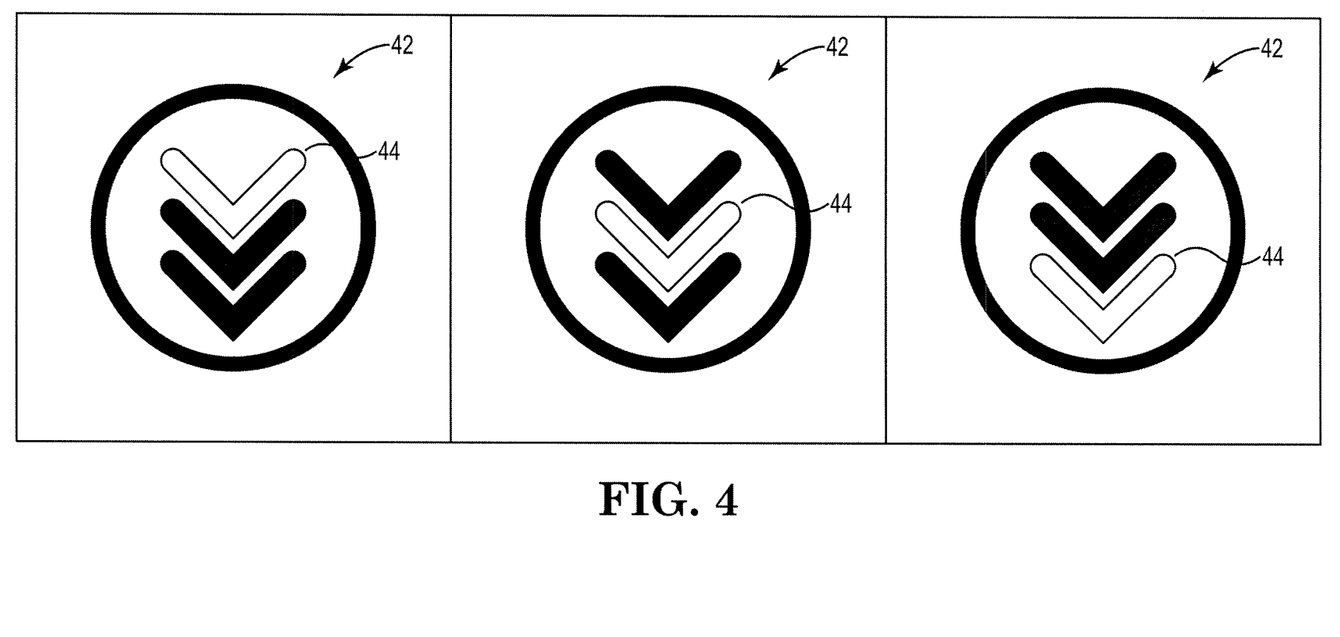
FIG. 4 depicts one aspect of the display means of FIG. 3.
Figure 5:
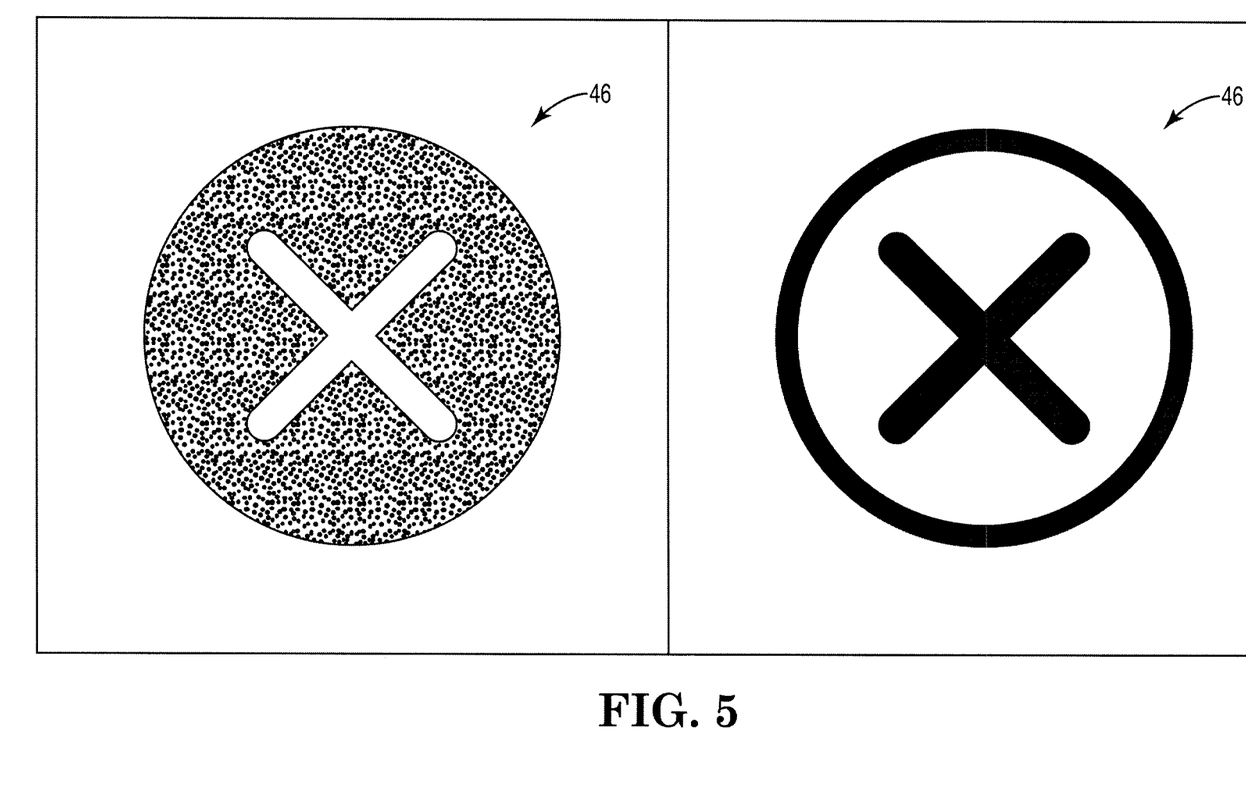
FIG. 5 depicts another aspect of the display means of FIG. 5.

FIG. 1 depicts one aspect of the system 10 in accordance with the invention. Those of skill in the art will appreciate that variations may be made without departing from the broad inventive concept disclosed herein. In a first aspect of the invention, the system 10 broadly includes a sound sensor 14, a peripherally inserted central catheter and monitoring means for monitoring the sound sensed by the sound sensor 18. The monitoring means may comprise a tablet, such as an iPad, that includes a display 22 having an animated indicator area 40. The animated indicator area 40 may include an arrow indicator, best seen in FIG. 4, that may include green colored backlit arrows 44 showing the progression of the catheter tip through the vascular system. The downward moving arrows would constantly repeat as the PICC progresses through the vascular system. Those of skill in the art will appreciate that the arrows 44 may be any color such as blue, yellow, and the like. FIG. 5 depicts one indicator in the form of an X that may be included on the display means that indicates visually indicates that there is a problem with the PICC moving through the vasculature. For example, the PICC may have encountered an obstruction, was navigated to a non-targeted area or has shifted out of position. The X indicator would provide a visual signal to the user that the user should stop progressing the catheter through the vasculature and that correction was needed. Those of skill in the art will appreciate that other symbols may be also be used such as a null symbol and that the symbol may be backlit and/or change color to indicate a problem with PICC navigation/placement.

The sound sensor 14 may comprise, by way of example, a microphone, pressure sensor or other types of sensors capable of sensing sound and known to those of skill in the art. In a first aspect of the invention, the sound sensor 14 senses the magnitude of the wave form generated by sound pressure. In other words, the sound sensor 14 is sensing the sound of the heart as the catheter progresses through the vein toward the heart.

As depicted in FIG. 1, sound sensor 14 is positioned within a housing 12. Housing 12 may be positioned on the saline column of a catheter 20 and is desirably water resistant or water proof. Housing 12 may be filled with any media capable of propagating sound pressure, which is sensed by the sound sensor 14, for example saline.

The sound sensor 14 is operably coupled to monitoring means 18 capable of measuring and displaying a graphical form of the sound. In one aspect, monitoring means 18 comprises a microprocessor that monitors and measures the magnitude of the wave form generated by sound pressure being sensed by the sensor 14. Voltages are recorded and displayed in graphical wave form and displayed on display means 22 to a user. Gradual increases in magnitude indicate to a user that the PICC is progressing toward the superior vena cava. Decreases in magnitude indicate to a user that the PICC has inadvertently been positioned in a non-target area or has shifted out of position or is obstructed.

Referring now to FIGS. 6-9 various display indicators and corresponding graphical acoustic wave forms are depicted to show progression of the PICC through the vasculature.

Figure 6:
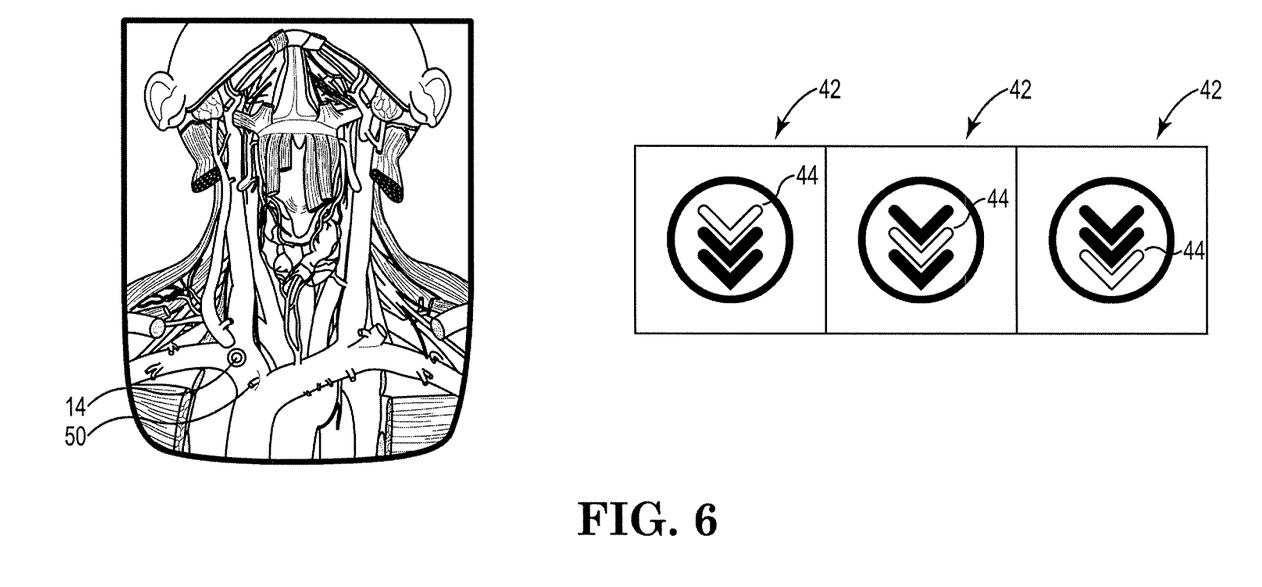
FIG. 6 depicts a bifurcation in the vascular system as the PICC is guided toward the heart and corresponding indicators on the display means.
Figure 7:
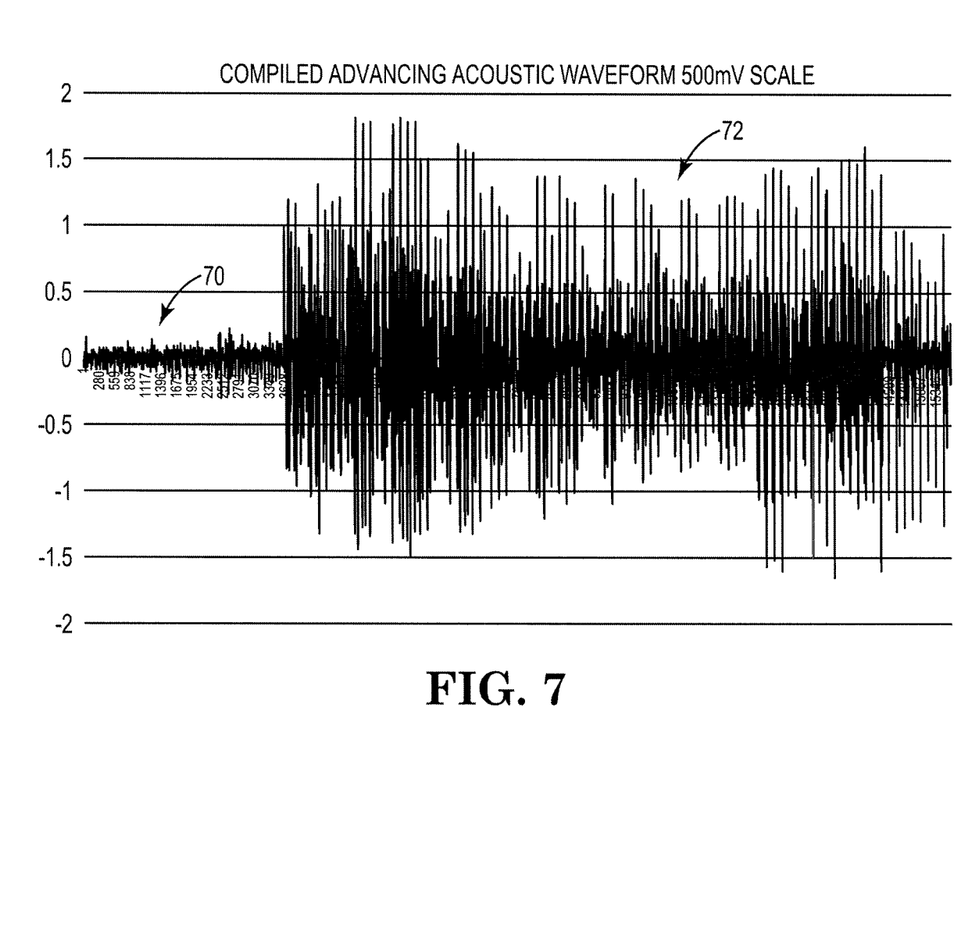
FIG. 7 depicts a misplacement of the PICC as it navigates through the vascular system and corresponding indicators on the display means.

FIG. 6 depicts a bifurcation 50 in the vascular system as the PICC is guided toward the heart. The display indicators 42 show the downward moving arrows 44 which indicate progression through the vasculature. Upon insertion of the PICC into the vascular system a low volume waveform 80 is displayed. As the PICC is advanced through the vasculature and nears the superior vena cava the sensor 14 senses a "high-volume" area 82 at the bifurcation due to the increases in sound pressure. The corresponding graphical acoustic wave form is shown in FIG. 7. As the PICC progresses through the vascular system a high volume acoustic wave form 82 is displayed indicating to a user that the PICC is progressing normally and is nearing the bifurcation and ready to be switched to ECG guidance. Arrows 44 on the display 22 would also indicate the progression of the PICC toward the bifurcation.

Figure 8:
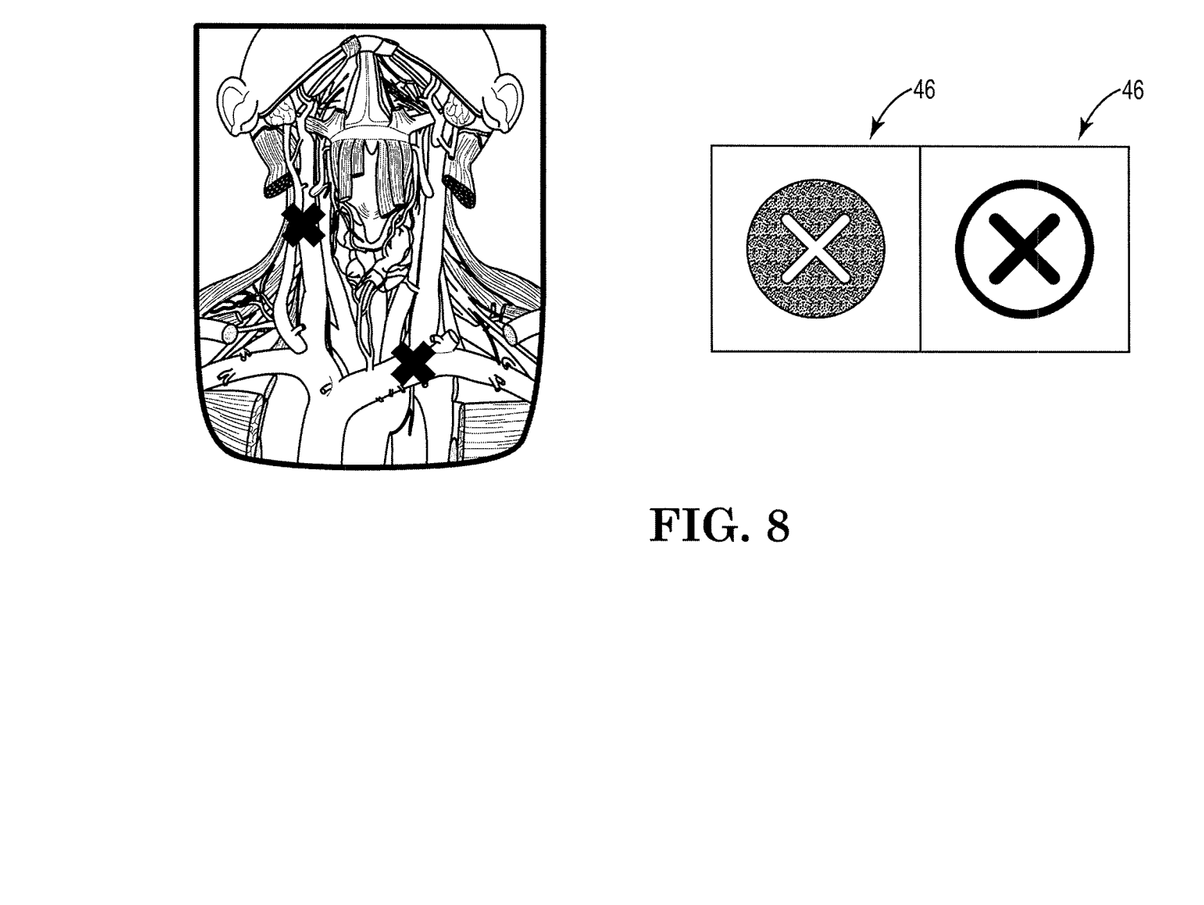
FIG. 8 depicts a graph displayed on the display means showing a high volume acoustic wave form indicating to a user that the PICC is progressing and nearing a desired bifurcation.
Figure 9:
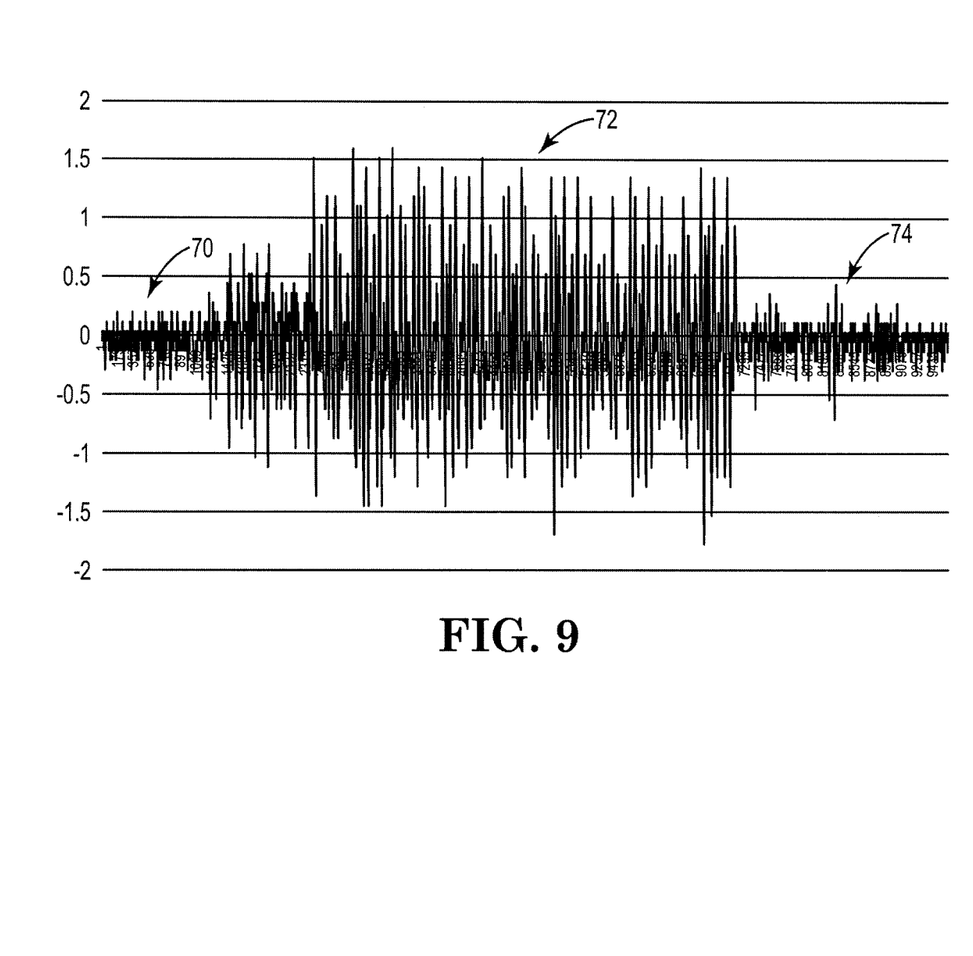
FIG. 9 depicts another acoustic wave form that may be displayed on the display means showing a low volume or "flat-line' acoustic wave form indicating to a user a misplacement of the PICC as it navigates through the vascular system.

Referring now to FIGS. 8 and 9, as the PICC is advanced through the vasculature it may become obstructed, advanced to a non-target area or has shifted out of position. The display indicator would indicate would indicate an X or other visual indicator 46, such as a null sign, that would indicate to the user that an issue occurred with the PICC and to stop advancing the PICC through the vasculature. The indicator 46 may be an X, may be colored red or some other color, may be blinking and/or may be other symbols known to those of skill in the art. Referring now to FIG. 9 the corresponding acoustic wave form may also be displayed on the display means. The low-volume area 70 is an indication of initial PICC placement. As the PICC is progressed through the vasculature a high-volume acoustic wave form 72 is seen indicating to a user that the PICC is nearing the correct target area. However, as the PICC is advanced an obstruction or misplacement is encountered and the acoustic wave form then reverts to a low-volume or "flat-line" wave form 74. A low-volume wave form 74 following immediately after a high-volume wave form 72 indicates the PICC is not progressing toward the targeted area.

Figure 2:
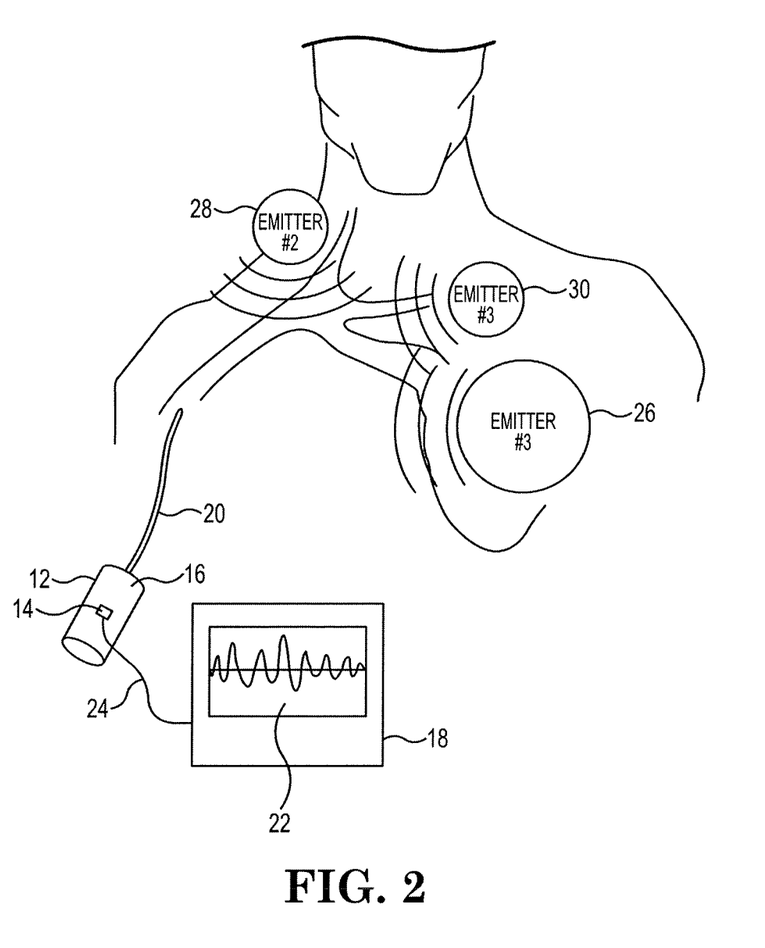
FIG. 2 depicts an alternative aspect of the present invention illustrating acoustic beacon emitters placed on various locations on a body.
Figure 3:
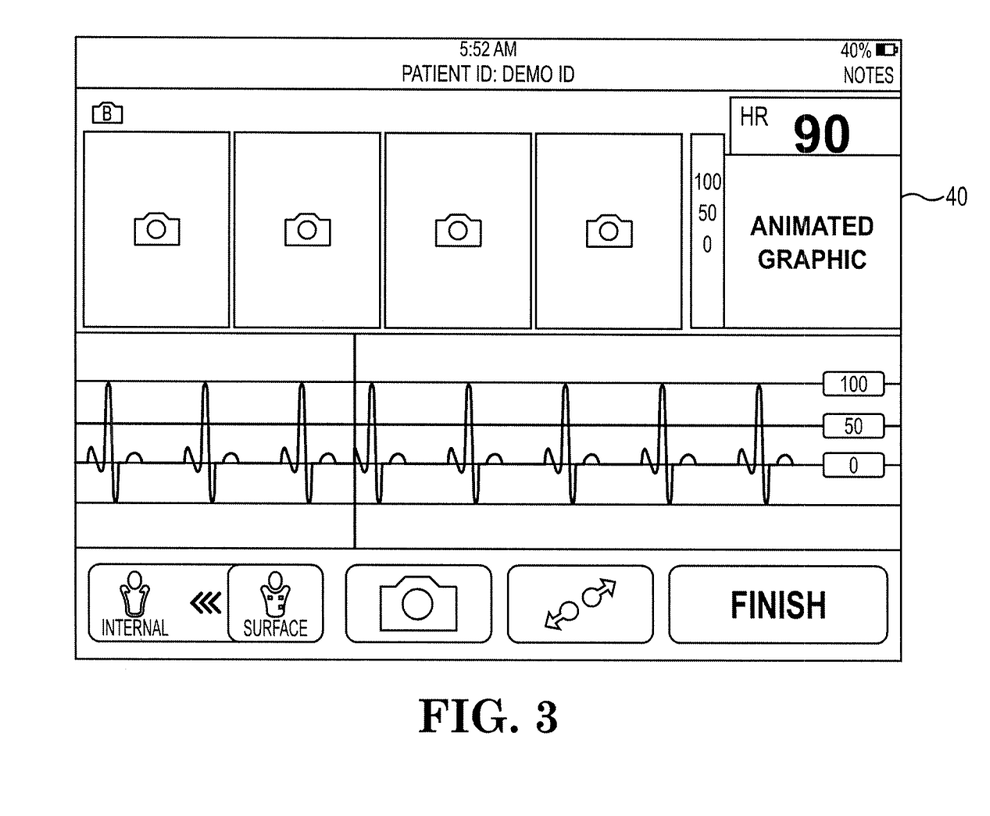
FIG. 3 depicts one aspect of a display means for displaying tracking of the PICC through the vasculature.

In an alternative embodiment, as seen in FIG. 2, the sound sensor 14 may be positioned on the tip of a PICC being inserted into a vein or on the saline column of the PICC and is designed to sense a heartbeat of an individual. The display means described above may also be used with the embodiment of FIG. 2.

In a further aspect of the invention, one or more acoustic sound emitters 26, 28, 30 may be placed at locations on the patient's body. One acoustic emitter 26 may be placed directly over the patient's heart to track the catheter tip as it nears the superior vena cava. The emitter 26 may utilize a specific frequency or sound to enable the user to distinguish it from other emitters 28, 30. Emitters 28, 30 may be placed on positions that are typically considered to be misplacement positions. The emitters 26, 28, 30 may also be used as triangulation devices by sending timed pulses or other signals that can be calculated by the sensor system to obtain the location of the catheter tip. Acoustic emitters 26, 28, 30 emit an acoustic beacon signal that are detected by the sound sensor 14 and displayed graphically on the display unit 22 of the monitoring means 18. While three acoustic beacon emitters are depicted, those of skill in the art will appreciate that fewer emitter may be utilized or any number of emitters may be used and depends on the number of catheter tip misplacement positions are possible.

It will be appreciated by those skilled in the art that changes could be made to the embodiment described above without departing from the broad inventive concept thereof. It is understood, therefore, that this invention is not limited to the particular embodiment disclosed, but it is intended to cover modifications within the spirit and scope of the present invention as defined by the appended claims.

What is claimed is:

1. A system comprising:
   a catheter comprising a catheter tip;
   at least one acoustic emitter to be positioned on a body of a patient, the at least one acoustic emitter to generate at least one acoustic beacon signal;
   a sound sensor operably coupled to the catheter, the sound sensor to detect a sound generated by a heart of the patient as the catheter tip is advanced toward the heart of the patient and to detect the at least one acoustic beacon signal; and
   a display unit operably coupled to the sound sensor; wherein the display unit is configured to graphically display a change in the sound generated by the heart and sensed by the sound sensor.

2. The system of claim 1 further comprising a housing for housing the sound sensor.

3. The system of claim 2 wherein said housing contains saline for propagating the sound generated by the heart.

4. The system of claim 2 wherein the catheter further comprises a saline column and the sound sensor is positioned on the saline column.

5. The system of claim 4 wherein said housing is positioned on the saline column of the catheter.

6. The system of claim 1 wherein the display unit further comprises a visual indicator to indicate a status of the catheter tip progression.

7. The system of claim 6 wherein the visual indicator comprises any of the following: an alphabetic character, an X, a downward arrow, a forward arrow, or a null-symbol.

8. The system of claim 1 wherein the sound sensor is positioned on the catheter tip.

9. The system of claim 1 wherein the sound sensor comprises a microphone.

10. The system of claim 1 wherein the display unit is configured to graphically display a change in the at least one acoustic beacon signal detected by the sound sensor.

11. A system comprising:
    a catheter comprising a tip;
    at least one acoustic emitter to be positioned on a body of a patient, the at least one acoustic emitter to generates at least one acoustic beacon signal;
    a sensor operably connected to the catheter and configured to sense a change in a magnitude of the wave form as the catheter tip is advanced toward a heart of the patient and to sense the at least one acoustic beacon signal; and
    a display unit operably connected to the sensor; wherein the display unit is configured to graphically display the change of the magnitude of a wave form sensed by the sensor.

12. The system of claim 11, wherein the sensor comprises a pressure sensor.

13. The system of claim 11, wherein the at least one acoustic emitter comprises at least three acoustic emitters.

14. The system of claim 11, further comprising a housing for housing the sensor; and wherein the catheter further comprises a saline column; and the housing is located on the saline column.

15. The system of claim 14, wherein the sensor is located on the catheter.

16. The system of claim 15, wherein the sensor is located on the catheter tip.

17. A system comprising:
    at least one acoustic emitter configured to be positioned over a heart on a body of a patient, the at least one acoustic emitter configured to generate at least one acoustic beacon signal;
    a sensor capable of being operably coupled to a catheter and configured to detect a change in a sound pressure as the catheter is advanced toward the heart and detect the at least one acoustic beacon signal; and
    a monitoring means operably coupled to the sensor; wherein the monitoring means is configured to graphically display a change in the sound pressure detected by the sensor and graphically display a change in the at least one acoustic beacon signal detected by the sensor.

18. The system of claim 17, wherein the sound pressure generates in part a magnitude of a wave form.

19. The system of claim 18, wherein the monitoring means further comprises a visual indicator configured to indicate a change in the magnitude of the wave form.

20. The system of claim 19, wherein the visual indicator is configured to depict an increase in the magnitude of the wave form that indicates to a user the catheter is advancing toward the heart; or wherein the visual indicator is configured to depict a decrease in the magnitude of the wave form that indicates to a user the catheter is advancing toward a non-target area or is obstructed.

* * * * *